United States Patent [19]

Blackburn et al.

[11] Patent Number: 4,968,323

[45] Date of Patent: Nov. 6, 1990

[54] METALWORKING FLUID COMPOSITION

[75] Inventors: Gary R. Blackburn, Washington Crossing, Pa.; Carl R. Mackerer, Pennington, N.J.

[73] Assignee: Mobil Oil Corporation, New York, N.Y.

[21] Appl. No.: 332,148

[22] Filed: Apr. 3, 1989

Related U.S. Application Data

[62] Division of Ser. No. 115,489, Nov. 2, 1987, abandoned.

[51] Int. Cl.$^5$ ............................................. C10L 1/18
[52] U.S. Cl. ................................................. 44/439
[58] Field of Search ............... 44/70, 79, 57; 252/54, 252/54.6, 78.1; 514/675; 72/236, 286; 208/18; 424/114, 723

[56] References Cited

U.S. PATENT DOCUMENTS

| | | | |
|---|---|---|---|
| 2,621,159 | 12/1952 | Perry et al. | 252/54.6 |
| 2,802,768 | 8/1957 | Meuli | 514/675 |
| 2,997,421 | 8/1961 | Hosmer et al. | 252/54.6 |
| 3,195,332 | 7/1965 | Ranauto | 72/236 |
| 3,833,731 | 9/1974 | Grier et al. | 514/526 |
| 3,877,922 | 4/1975 | Grier et al. | 514/526 |
| 4,086,066 | 4/1978 | McDermott | 44/51 |
| 4,215,075 | 7/1980 | Magee | 564/255 |
| 4,462,820 | 7/1984 | Grade et al. | 44/72 |
| 4,585,462 | 4/1986 | Kitchen, III | 44/72 |
| 4,626,543 | 12/1986 | Kollmeyer | 514/365 |
| 4,708,720 | 11/1987 | Grangette et al. | 44/51 |

*Primary Examiner*—Margaret B. Medley
*Attorney, Agent, or Firm*—A. J. McKillop; C. J. Speciale; M. J. Mlotkowski

[57] ABSTRACT

1-Bromopinacolone is a microbial biocide that is highly effective in suppressing the growth of bacteria, fungi and algae which can occur during storage and use of hydrocarbon oils including gasoline, jet fuel and heating oil. It is particularly effective in emulsifiable oils for metal working, such as cutting oils and rolling oils.

8 Claims, No Drawings

METALWORKING FLUID COMPOSITION

This is a divisional of application Ser. No. 115,489, filed on Nov. 2, 1987, now abandoned.

FIELD OF THE INVENTION

This invention is concerned with the use of 1-bromopinacolone as a biocide and/or preservative in hydrocarbon fuels and metalworking hydrocarbon fluids.

BACKGROUND OF THE INVENTION AND PRIOR ART

A very large number of industrial processes and products are adversely affected when contaminated by microorganisms followed by their subsequent growth. The ubiquitous nature of these microorganisms, which include numerous bacteria, fungi and algae, make prevention of such contamination impractical. However, the practical alternative of including in the product, or of adding to the process, an antimicrobial agent has become very widespread. As used herein, the term "microorganisms" applies to bacteria, fungi, and algae, and mixtures thereof. The mode of action of these compounds, in many cases speculative, appears to vary and includes mechanisms such as interference with the permeability of the cytoplasmic cell membrane, precipitation and/or modification of the cell proteins, and interference with an enzyme system. Regardless of chemical type or of mode of action, it is a practical requirement for an industrial antimicrobial agent that it be effective at very low concentrations, in order that it control the growth of the offending microorganisms without encountering excessive cost or imparting an undesirable property to the process or product, such as creating a health hazard. In practice, a given antimicrobial agent may either destroy all of the contaminating cells present or it may simply prevent their further proliferation to an extent that would be harmful to the substrate or to the system being protected.

The fields of application for industrial anti-microbial agents include cosmetics, disinfectants, wood preservation, manufacture of food and animal feeds, manufacture of paint, especially emulsion paints, cooling water treatment, manufacture of plastics and resins, pulp and paper manufacture, textile manufacture and printing, adhesives, petroleum production and refining, and others. In the petroleum industry, biocides are used to control the growth of bacteria in drilling muds, and to control the bacterial, fungal and algal slimes in industrial recirculating cooling water. They are also added to petroleum products since many of these are stored in tanks under circumstances which permit the accumulation of a layer of water at the bottom of the storage tank. Microbial growth which can take place under these circumstances, probably at the interface, leads to contamination of the fuel with solid matter which can plug mechanical filters. A plugged filter at the point of use can cause shutdown of the burner or engine fed by the fuel. Thus, biocides are added to home heating oil, to diesel fuel and to jet fuel. Petroleum products such as metalworking fluids, which are emulsifiable, are also protected against subsequent degradation by the addition of antimicrobial agents.

A review of the various types of organic compounds that have been found useful as industrial antimicrobial agents, and of their industrial applications, is found in "Encyclopedia of Chemical Technology", Kirk-Othmer, 3rd Edition, Volume 13, John Wiley & Sons, New York, N. Y. pp. 224–251, (1981), the entire content of which is incorporated herein by reference for background purposes.

U.S. Pat. No. 3,833,731 to Grier et al. describes the use of 2-halo-2-halomethyl glutaronitriles as antibacterial and antifungal agents. U.S. Pat. No. 3,877,922 issued to Grier describes the use of the same compounds to control the growth of algae. U.S. Pat. No. 4,462,820 to Grade and Lorenz describe the use of mono- and di-bromodicyanomethane as industrial biocides. U.S. Pat. No. 2,802,768 to Meuli discloses an agronomical practice in which fungus infected soil is treated with a haloketone having the formula

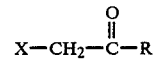

wherein X is chlorine or bromine and R is an alkyl radical having two to four carbon atoms.

BRIEF SUMMARY OF THE INVENTION

This invention is based on the discovery that 1-bromopinacolone

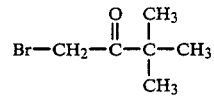

is a wide-spectrum biocide of very high potency with respect to both bacteria and fungi. Liquid hydrocarbon fuels and metalworking fluids that comprise liquid hydrocarbons are subject to fouling and/or to deterioration due to the growth of contaminating microorganisms. Such fuels and metalworking fluids are beneficially altered by contacting the microorganisms with a biocidally effective amount of 1-bromopinacolone.

In such compositions or processes, the bromopinacolone may be the sole biocidal agent. However, it is contemplated in certain instances to utilize the bromopinacolone in combination with one or more known antimicrobial agents, as more fully explained herein below.

Metalworking fluids, particularly emulsifiable (or soluble) cutting oils and rolling oils, are very effectively protected from fouling by the use of bromopinacolone, as will be hereinunder illustrated by example.

DETAILED DESCRIPTION, SPECIFIC EMBODIMENT AND BEST MODE

As used herein, the terms "biocide", "antimicrobial", "bactericide", "algacide", and the like are intended to encompass control of bacteria (both aerobic and anaerobic), fungi, and algae broadly and to include killing as well as inhibiting the growth of such organisms.

1-Bromopinacolone is a known compound which is commercially available. It may be prepared by the bromination of pinacolone, which in turn is prepared by the classical rearrangement of pinacone.

Based on the effectiveness observed in the Examples given below, it is contemplated that the antimicrobial activity of bromopinacolone is effective against contaminating microorganisms such as bacteria, including *Aerobacter sp.* such as *A. aerogenes*, *Bacillus sp.* such as *B. bycoides*, *Pseudomonas sp.* such as *P. aeruginosa*, Staphylococcus sp. such as *S. aureus*, Escherichia sp. such as *E. coli*, Cellulomonas sp. such as *C. biazotea*. Proteus sp. such as *P. mirabilis*, and sulfate reducing bacteria including Desulfovibrio sp., such as *D. desulfuricans*. Other organisms include fungi such as Rhodotorula sp., Alternaria sp., Aspergillus sp. such as *A. niger*, Pullularia sp. such as *P. pullulans*, Penicillioum sp. such as *P. luteum*, Chaetomium sp. such as *C. globosum*, Trichoderma sp. such as *T. virde*, Rhizoctonia sp. such as *R. solani*. Such bateria and/or fungi commonly are found on cereal and grain products, on oils, on fruits and vegetables and on cosmetics, leather, electrical insulation, textiles and numerous other materials capable of supporting their growth such as on plants, seeds, fur, wood and in soils. It is contemplated that bromopinacolone is effective against the mold *Cladosporium resinae* which grows in hydrocarbon oil storage tanks.

Depending on the intended application, it is to be understood that bromopinacolone, which is liquid at room temperature, may be introduced into the substance or material to be treated in any one of a number of forms. It may be employed neat, or it may be prepared as an adsorbate on a suitable inert carrier such as talc, clay, diatomaceous earth and the like, or it may be prepared as a solution in a solvent, as an emulsion, a suspension, a concentrate, an emulsifiable concentrate, and the like, depending on circumstances and the material to be treated. It is contemplated further that bromopinacolone may be used in admixture with other antimicrobial materials, in special instances with marked advantage. It may be introduced before contamination or after contamination by the offending microorganisms, and it may be introduced as a single treatment (single dose), or periodically as needed for effective control. The amount introduced will of course depend on the particular application, and when used as the sole biocide the amount will be that needed for the effective control. However, the material is unusually effective, and in general amounts up to about 100 ppm will be found to give adequate control.

1-Bromopinacolone is particularly effective when used in preventing or mitigating the effects of microbial contamination in metalworking fluids.

Metalworking fluids are extensively used in the cutting, forming and heat treatment of metals, in which instances they are called "cutting oils", "rolling oils'-'and "quenching oils", resp. An important functional constituent of metalworking fluids is a hydrocarbon oil, but other organic compounds such as emulsifiers are often present.

Cutting oils are sold usually as water-dilutable, emulsifiable (or soluble) oils which are mixed with water and put into a resevoir tank at the point of use. Material is withdrawn from the tank and furnished to the cutting tools as needed, after which it is returned to the storage tank. Lacking treatment, spoilage soon sets in with the development of foul odor and sludge which can interfere with the filtration to remove metal chips in recycled oil. As shown by the examples given below, 1-bromopinacolone is an effective biocide in such system. The 1-bromopinacolone is added to the emulsifiable cutting oil either prior to dilution with water, after dilution with water, or in some instances both before and after dilution.

Some rolling oils are emulsifiable and are intended for use with a certain amount of water for its coolant effect. Problems similar to those encountered with cutting oils arise in the reservoir tank. Other metalworking fluids, such as quenching oils, although not intended to be used in emulsified form, may come into contact with water during use and give rise to fouling. In all of such instances, 1-bromopinacolone is an effective agent for suppressing such fouling.

EXAMPLES

The following examples are given for illustrative purposes only, and are not to be construed as limiting the scope of the invention, which scope is determined by this entire specification including appended claims. All amounts and proportions are by weight unless explicitely stated to be otherwise.

EXAMPLE 1

This example illustrates the effectiveness of bromopinacolone in a spot test.

An overnight broth culture of the bacteria present in used cutting oil was prepared by inoculating 0.1 ml of contaminated emulsion into 25 ml of Oxoid 2 Nutrient Broth, and allowing growth to proceed for 24 hours at 30° C. One-tenth ml of this culture, containing $3 \times 10^9$ bacteria was then added to 2 ml of top agar, which in turn was overlayered on a Nutrient Agar plate. When the top agar had solidified, a sterile filter-paper disc containing the brompinacolone was placed on the top agar surface. The plate was incubated at 30° C. for 12 hours, after which time no growth whatsoever was noted, i.e., the entire plate was sterilized.

What is claimed is:

1. A fuel composition comprising a liquid hydrocarbon fuel and biocidally effective amount of 1-bromopinacolone, whereby said 1-bromopinacolone is effective to suppress bacterial growth in said liquid hydrocarbon fuel.

2. The composition described in claim 1 wherein said liquid hydrocarbon fuel is a diesel fuel.

3. The composition described in claim 1 wherein said liquid hydrocarbon fuel is a home heating oil.

4. The composition described in claim 1 wherein said liquid hydrocarbon fuel is a jet fuel.

5. The composition described in claim 1 wherein said 1-bromopinacolone is present in an amount of up to about 100 ppm.

6. The composition described in claim 2 wherein said 1-bromopinacolone is present in an amount of up to about 100 ppm.

7. The composition described in claim 3 wherein said 1-bromopinacolone is present in an amount of up to about 100 ppm.

8. The composition described in claim 4 wherein said 1-bromopinacolone is present in an amount of up to about 100 ppm.

* * * * *